(12) United States Patent
Prasad et al.

(10) Patent No.: US 10,325,767 B1
(45) Date of Patent: Jun. 18, 2019

(54) FAIMS DEVICE FOR SEPARATION OR TRANSMISSION OF IONS

(71) Applicant: Thermo Finnigan LLC, San Jose, CA (US)

(72) Inventors: Satendra Prasad, San Jose, CA (US); Michael W. Belford, Los Altos, CA (US); Jean-Jacques Dunyach, San Jose, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 0 days.

(21) Appl. No.: 15/916,621

(22) Filed: Mar. 9, 2018

Related U.S. Application Data

(60) Provisional application No. 62/469,016, filed on Mar. 9, 2017.

(51) Int. Cl.
*G01N 27/62* (2006.01)
*H01J 49/00* (2006.01)

(52) U.S. Cl.
CPC .......... *H01J 49/004* (2013.01); *G01N 27/624* (2013.01)

(58) Field of Classification Search
CPC ............................ H01J 49/004; G01N 27/624

USPC ....... 250/281, 282, 286, 287, 288, 290, 291, 250/292, 293

See application file for complete search history.

(56) References Cited

U.S. PATENT DOCUMENTS 6,639,212 B1  10/2003  Guevremont et al.

*Primary Examiner* — Nicole M Ippolito
*Assistant Examiner* — Hanway Chang
(74) *Attorney, Agent, or Firm* — A.J. Gokcek

(57) ABSTRACT

A FAIMS device interfaces between an ionization source and a mass spectrometer. The FAIMS device includes inner and outer electrodes having radially opposed surfaces, which define there between a gap through which ions are transported. A waveform generator is configured to apply a selected one of two distinct periodic waveforms to the electrodes, consisting of: a first waveform characterized by equal high and low amplitudes and periods and a second waveform including a bi-sinusoidal waveform superimposed with a DC compensation voltage. The device is configured to toggle between a transmission mode of operation in which ions are passed through the device with no spatial separation when the first waveform is applied to the inner and/or outer electrodes and a separation mode of operation in which spatial separation of the ions occurs in the gap when the bi-sinusoidal waveform and DC voltage are applied to the inner and/or outer electrodes.

20 Claims, 8 Drawing Sheets

FAIMS DEVICE FOR SEPARATION OR TRANSMISSION OF IONS

CROSS-REFERENCE TO RELATED APPLICATION

This application claims the priority benefit under 35 U.S.C. § 119(e) of U.S. provisional patent application No. 62/469,016 entitled "Symmetrical FAIMS Waveform" filed on Mar. 9, 2017, the disclosure of which is incorporated herein by reference.

FIELD OF THE INVENTION

This invention relates to high field asymmetric waveform ion mobility spectrometry (FAIMS). More specifically, this invention relates to a FAIMS device configured to toggle between a separation mode of operation and a transmission mode of operation.

BACKGROUND OF THE INVENTION

In ion mobility spectrometry devices, separation of gas-phase ions is accomplished by exploiting variations in ion drift velocities under an applied electric field arising from differences in ion mobility. One well-known type of ion mobility spectrometry device is the High Field Asymmetric Waveform Ion Mobility Spectrometry (FAIMS) cell, also known by the term Differential Ion Mobility Spectrometry (DMS) cell, which separates ions on the basis of a difference in the mobility of an ion at high field strength (commonly denoted as $K_h$) relative to the mobility of the ion at low field strength (commonly denoted as $K_l$). FAIMS cells may be used for a variety of purposes, including providing filtering of ions prior to entry into a mass analyzer.

Briefly described, a FAIMS cell or device comprises a pair of cylindrical electrodes separated by an annular space that defines an ion separation region through which ions are passed. During transit, ions in the separation gap experience an alternating electric field created using a bi-sinusoidal radio frequency (RF) waveform. The bi-sinusoidal waveform is a composite of a sine waveform and its scaled phase shifted harmonic. Ions oscillating between the high and low period of the bi-sinusoidal waveform can exert different electrical mobility. For instance, the electrical mobility of some ions can be higher during the high period of the waveform compared to the low period of the waveform. Ions of such mobility behavior in FAIMS are classed as A type ions and owing to their positive displacement over a single RF cycle, an A type ion can deviate away from the inner RF applied electrode and annihilate on the outer electrode over multiple RF cycles of the waveform. However, a DC offset (compensation voltage, or CV) can be applied to the electrode (inner bias) to correct for the trajectory of an A type ion such that the ion can be transmitted through the FAIMS device. Alternatively, a time-varying set of ions can be transmitted by sweeping the CV and generating a FAIMS spectrum ion current versus CV.

SUMMARY

The present invention includes devices and methods of transmitting and/or separating ions using a FAIMS device. In one embodiment of the present invention, a FAIMS device is provided that interfaces between an ionization source and a mass spectrometer, and may operate at or near atmospheric pressure. The device includes an inner and an outer electrode having radially opposed surfaces, which define a gap through which ions are transported. The device also includes a RF waveform generator configured to apply a selected one of two distinct periodic RF waveforms to the electrodes, consisting of: a first waveform characterized by equal high and low voltage amplitudes and periods, and a second RF waveform comprising a bi-sinusoidal waveform superimposed with a DC compensation voltage. The device is configured to toggle between a transmission mode of operation in which ions are passed through the device with no spatial separation when the first waveform is applied to the inner and/or outer electrodes and a separation mode of operation in which spatial separation of the ions occurs in the gap when the bi-sinusoidal waveform and DC voltage are applied to the inner and/or outer electrodes.

In some embodiments, the toggling between the transmission and separation modes of operation occurs over the course of a liquid chromatography-high-field asymmetric waveform ion mobility spectrometry-mass spectrometry (LC-FAIMS-MS) analysis.

During the transmission (i.e., no ion separation) mode, a precursor scan can be visualized for all the ions from the ionization source, providing an instantaneous view of the precursor ions at any point along an LC gradient with ion abundances comparable to LC-MS thus eliminating the need to uninstall FAIMS hardware from the mass spectrometer.

In certain embodiments, during the transmission mode, RF heating of the ions may be induced by varying operational parameters until dissociation of fragile adducts or fragmentation of precursor ions to product ions occurs in the device. The varied parameters may be one or more of the following: inner and/or outer electrode temperature, waveform voltage amplitude, and frequency. Another parameter that impacts ion heating or fragmentation efficiency is the period the ions are exposed to ion heating or fragmentation conditions. It is termed as the ion transit time through the FAIMS device and can be approximately 50 milliseconds (ms), depending on the ion flight path and linear speed of the FAIMS ion transport gas.

During transit in the FAIMS device, ions experience a desolvation mechanism similar to that existing in a heated mass spectrometer (MS) inlet. A key advantage with the FAIMS device is the extended period ions experience the desolvation condition: approximately 50 ms in FAIMS versus less than 1 ms in the mass spectrometer inlet. In addition, when a FAIMS electrode is applied a RF waveform configured for transmission mode, ions experience RF heating that acts as a desolvation mechanism. The two heating mechanisms can be seen as a feature available in a FAIMS transmission mode and can significantly benefit applications that suffer from poor desolvation such as application studying native assembly of proteins where ions are generated using high salt concentration and aqueous medium.

In another embodiment, during the transmission mode, all ions are transmitted through the device for purposes of calibrating the mass spectrometer instrument without interrupting or stopping ion production.

In some embodiments, the first waveform is a sine wave.

In some embodiments, both precursor ions and product ions are simultaneously transmitted through the device.

In another embodiment of the present invention, a method of transmitting and/or separating ions using a FAIMS device is provided that interfaces between an ionization source and a mass spectrometer and may operate at or near atmospheric pressure. The method includes providing inner and outer electrodes having radially opposed surfaces, which define there between a gap through which ions are transported. The method also includes configuring two distinct periodic waveforms applied to the electrodes, consisting of: a first waveform characterized by equal high and low amplitudes and periods and a second waveform comprising a bi-sinusoidal waveform superimposed with a DC compensation voltage. The method further includes toggling between a transmission mode of operation in which ions are passed through the device with no spatial separation when the first waveform or sine wave is applied to the inner and/or outer electrodes and a separation mode of operation in which spatial separation of the ions occurs in the gap when the bi-sinusoidal waveform and DC voltage are applied to the inner and/or outer electrodes.

DETAILED DESCRIPTION OF EMBODIMENTS

Figure 1:
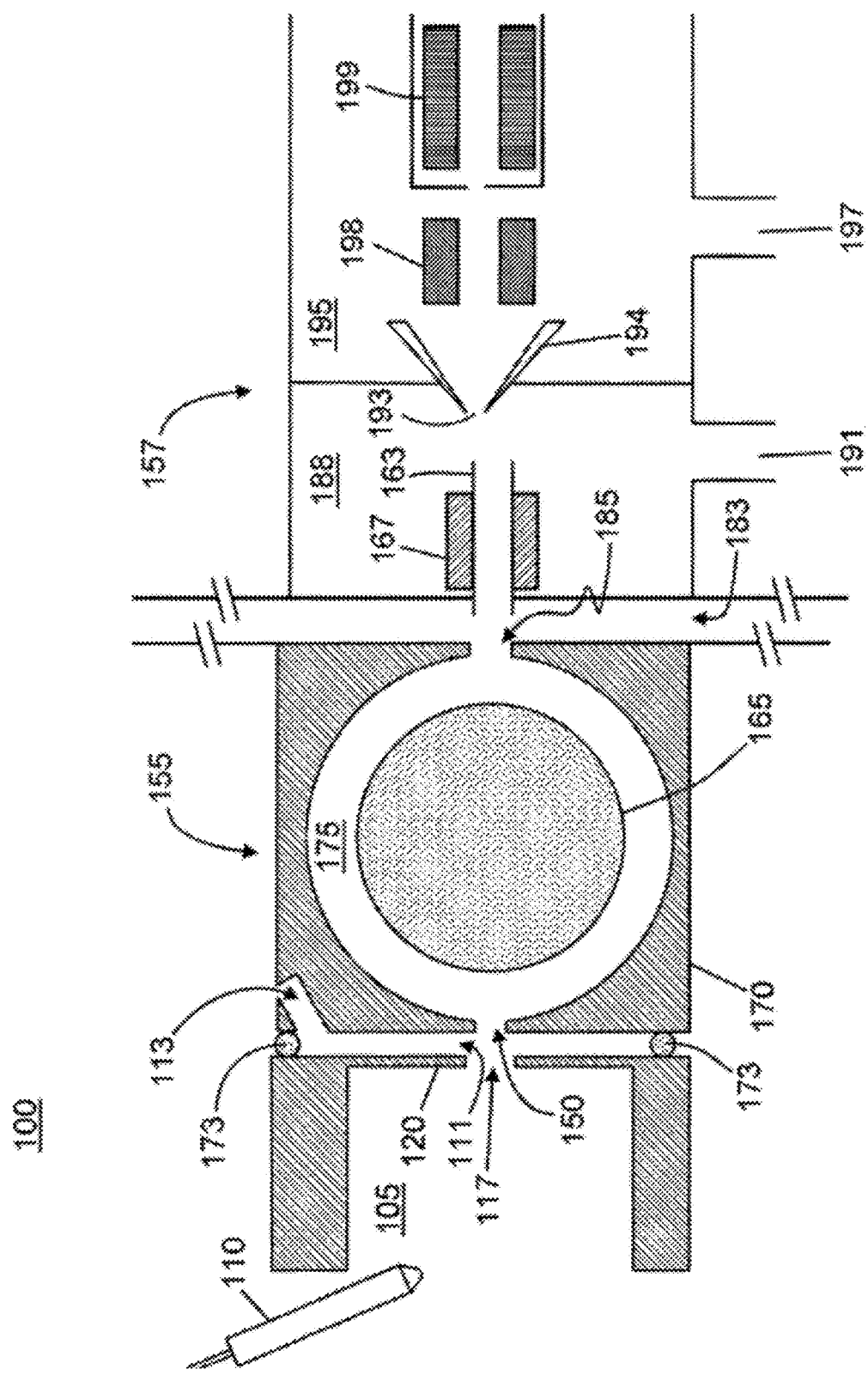
FIG. 1 schematically depicts a system for analyzing ions that includes a FAIMS device which may be configured in accordance with methods and devices embodying the present invention.

FIG. 1 schematically depicts a system 100 for analyzing ions that includes a FAIMS device 155. A solution of sample to be analyzed is introduced as a spray of liquid droplets into an ionization chamber 105 via atmospheric pressure ion source 110. Ionization chamber 105 is maintained at a high pressure relative to the regions downstream in the ion path, typically at or near atmospheric pressure. Atmospheric pressure ion source 110 may be configured as an electrospray ionization (ESI) probe, wherein a high DC voltage (either positive or negative) is applied to the capillary or "needle" through which the sample solution flows. Other suitable ionization techniques may be utilized in place of ESI, including without limitation such well-known techniques as atmospheric pressure chemical ionization (APCI), heated electrospray ionization (HESI), and thermospray ionization.

Ions produced by the ion source enter the FAIMS cell 155 through an aperture 117 in an entrance plate 120 and then through an inlet orifice 150 after passing through an expansion chamber 111. The expansion chamber is provided with a gas, typically helium or other inert gas, which is introduced into the expansion chamber 111 via a gas conduit 113. A portion of the gas flows back into the ionization chamber 105 through entrance plate aperture 117 in counter-flow to the ions and droplets and serves to desolvate charged droplets. Another portion of the gas combines with the analyte ions in chamber 111 and serves as a carrier gas through the FAIMS cell 155. The combined ion/carrier gas flow then enters FAIMS cell 155 through inlet orifice 150. The carrier gas flow may be carefully metered to maintain flow rates within predetermined limits which will depend on the FAIMS cell size, electrode geometry, and operational considerations. An electrical potential difference is maintained between the entrance plate 120 and the FAIMS cell 155 and, thus, physical separation is maintained between these components. Accordingly, a non-conducting sealing element 173, such as a gasket or P-ring maintains the FAIMS gas within the apparatus and prevents contamination of this gas from outside air. Because of drawing-space limitations, this sealing element is not explicitly shown in some of the accompanying drawings.

Figure 8:
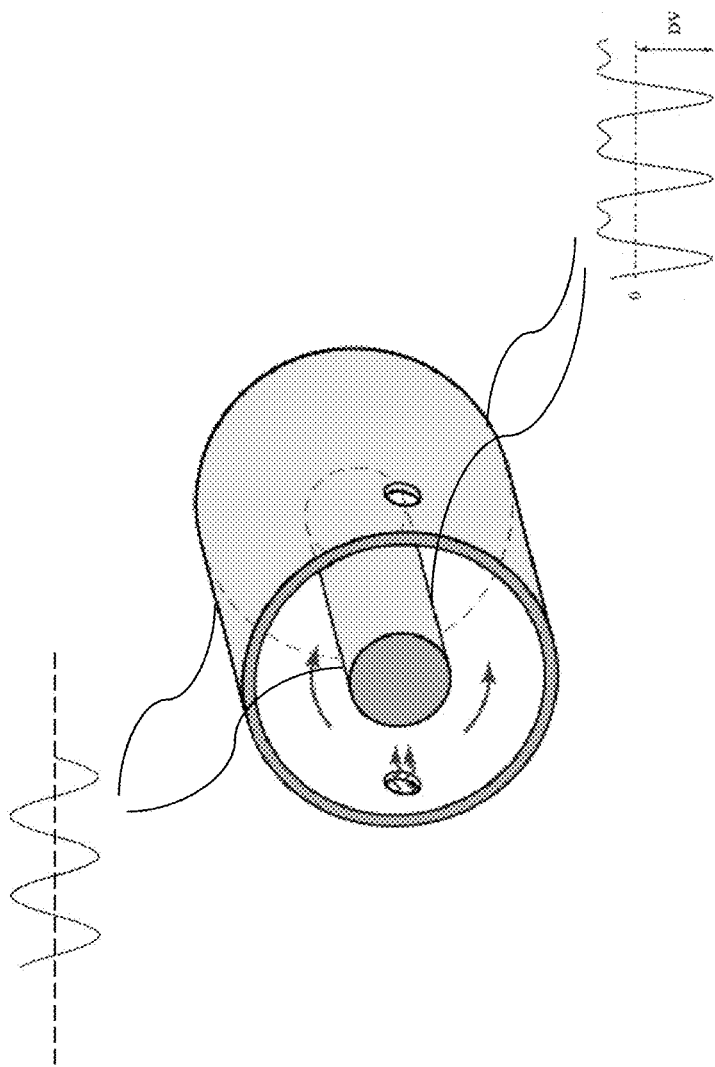
FIG. 8 depicts waveform generators, one for transmission mode and the other for separation mode, applied to inner and/or outer electrodes of the FAIMS device, in accordance with one embodiment of the present invention.

Generally speaking, the FAIMS cell 155 includes inner and outer electrodes 165 and 170 having radially opposed surfaces, which define there between an annular separation region 175 (an "analytical gap") through which the ions are transported. The FAIMS cell geometry depicted in FIG. 1 may be generally referred to as a "side-to-side FAIMS cell", in which the longitudinal axes (axes of cylindrical surfaces, directed out of the page) of inner electrode 165 and outer electrode 170 are oriented transversely with respect to the overall direction of ion flow. The principles of the design and operation of FAIMS cells and other ion mobility spectrometry devices have been extensively described elsewhere in the art (see, for example, U.S. Pat. No. 6,639,212 to Guevremont et al.), and hence will not be described in detail herein. In brief, the carrier gas and ions flow through the separation region 175 from inlet orifice 150 to exit orifice 185. Ion separation is effected within the separation region (analytical gap) 175 of the FAIMS cell 155 by applying an asymmetric waveform having a peak voltage (DV) and a compensation voltage (CV) to one of the inner or outer electrodes, 165, 170. The values of CV and DV are set to allow transmission of a selected on species through separation region 175. Other ion species having different relative values of high field and low field mobilities will migrate to the surface of one of the electrodes and be neutralized. In FAIMS transmission mode, a waveform characterized by equal high and low amplitudes and periods is applied to the inner or outer electrodes. An example of a waveform generator, which is configured to apply a selected one of these two distinct periodic waveforms to the electrodes, is shown in FIG. 8.

Still referring to FIG. 1, the selected ions emerge from the FAIMS cell 155 through exit orifice 185 and pass through a small gap 183 separating the FAIMS cell 155 from a mass spectrometer 157. Whereas most of the carrier gas exhausts through the gap 183 at atmospheric pressure, ions are electrostatically guided into at least one reduced pressure chamber 188 of the mass spectrometer 157 through an orifice in the mass spectrometer or through a capillary inlet or ion transfer tube 163. The at least one reduced pressure chamber may be evacuated by a vacuum port 191. At least a portion of ion transfer tube 163 may be surrounded by and in good thermal contact with a heat source, such as heater jacket 167. The heater jacket 167, which may take the form of a conventional resistance heater, is operable to raise the temperature of ion transfer tube 163 to promote further desolvation of droplets entering the ion transfer tube 163.

From the at least one reduced pressure chamber 188, ions are transferred through an orifice 193 of a skimmer 194 into a high vacuum chamber 195 maintained at a low pressure (typically around 100 millitorr) relative to the reduced pressure chamber 188. The high vacuum chamber 195 is typically evacuated by turbo or similar high-vacuum pumps via a vacuum port 197. The skimmer 194 may be fabricated from an electrically conductive material, and an offset voltage may be applied to skimmer 194 to assist in the transport of ions through interface region and into skimmer orifice 193. Ions passing through skimmer orifice 193 may be focused or guided through ion optical assembly 198, which may include various electrodes forming ion lenses, ion guides, ion gates, quadrupole or octopole rod sets, etc. The ion optical assembly 198 may serve to transport ions to an analyzer 199 for mass analysis. Analyzer 199 may be implemented as any one or a combination of conventional mass analyzers, including (without limitation) a quadrupole mass analyzer, ion trap, or time-of-flight analyzer.

Figure 2:
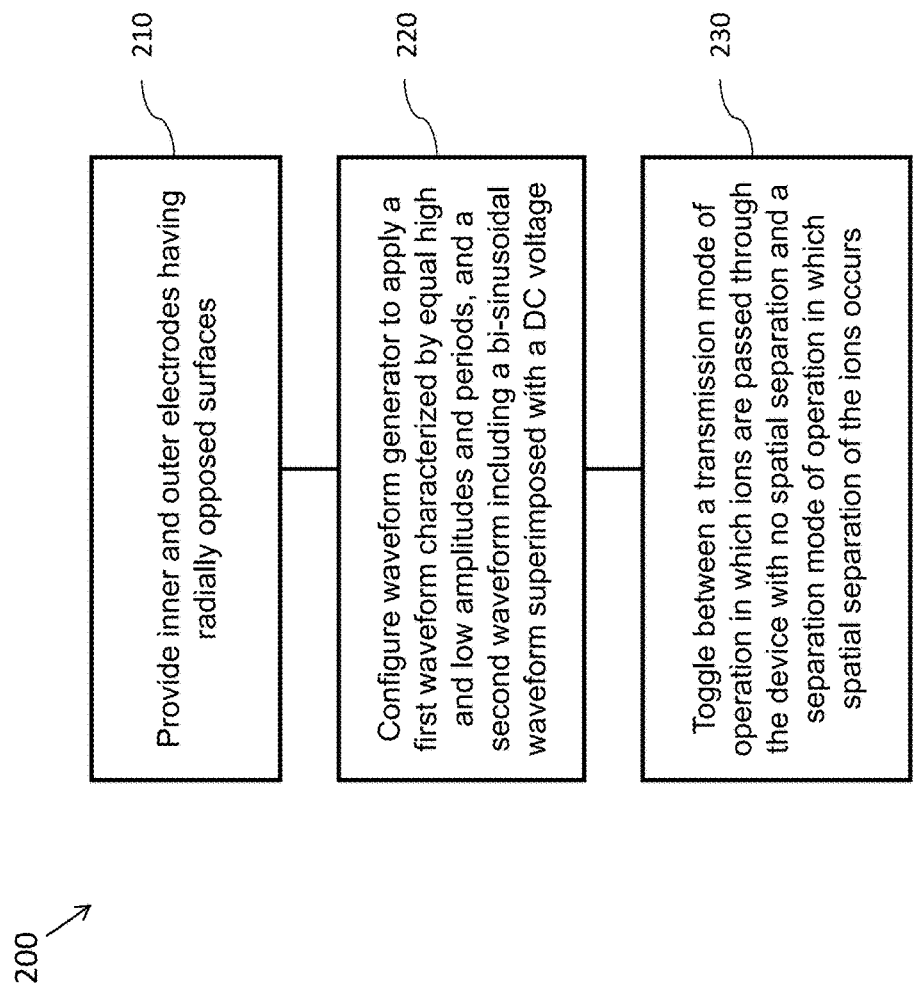
FIG. 2 is a flowchart depicting steps of a method of transmitting and/or separating ions using a FAIMS device, in accordance with one embodiment of the present invention.

FIG. 2 is a flowchart depicting steps of a method of transmitting and/or separating ions using a FAIMS device described herein that interfaces between an ionization source and a mass spectrometer and operates at atmospheric pressure, in accordance with one embodiment of the present invention. In Step 210, inner and outer electrodes having radially opposed surfaces are provided. An annular region or gap through which ions are transported is between the inner and outer electrodes. In Step 220, a waveform generator configured to apply a selected one of two distinct periodic waveforms to the electrodes, consisting of: a first waveform characterized by equal high and low amplitudes and periods and a second waveform comprising a bi-sinusoidal waveform superimposed with a DC compensation voltage. In Step 230, toggling occurs between a transmission mode of operation in which ions are passed through the device with no spatial separation when the sine wave is applied to the inner and/or outer electrodes and a separation mode of operation in which spatial separation of the ions occurs in the gap when the bi-sinusoidal waveform and DC voltage are applied to the inner and/or outer electrodes.

FAIMS can be operated in a "no ion separation mode" or "ion transmission mode" with a symmetrical sine waveform where the voltage amplitude can be between 0 to −5000 V or 0 to +5000 V and the frequency between 1 MHz to 6 MHz to pass all the ions from the ion source to a mass spectrometer. The selection of voltage amplitude and frequency will be partially determined by the mobility of ions. In general high mobility ions will require less voltage amplitude and higher frequency to allow amplitude of oscillation less than the ion separation gap. Ion oscillation exceeding the ion separation gap will yield poor ion transmission. Owing to the sine waveform, the electrical mobilities of ions during the high and low period of the waveform are equal. Ions oscillate around a center axis with a spatial displacement that is equal in the high and low period of the sine waveform. With no net displacement over a RF cycle or multiple RF cycles, no spatial separation of ions occur, eliminating the need for a CV to transmit ions.

Such mode of operation (no ion separation mode) does not promote ion separation but may offer multiple advantages to selected applications. The transmission mode can provide a convenient way to pass all the ions in a calibrant to the MS without the need to uninstall the FAIMS device and interrupt ion production. A user could rapidly check and calibrate the MS without detaching FAIMS from the instrument.

Another advantage may be the ability to alternate between transmission and separation mode over the course of a Liquid Chromatography-FAIMS-Mass Spectrometry (LC-FAIMS-MS) analysis. By switching to transmission mode, a user can rapidly visualize the ion distribution in a mass spectrometry single quadrupole (MS Q1) full scan for all the ions from the ion source. The result is a quick "snapshot" of high abundance pre-cursors at any point along the LC gradient and is near equal to generating a LC-MS MS Q1 full scan without FAIMS. Although, the same can be achieved by setting the amplitude (V) of a bi-sinusoidal waveform to zero and relying on FAIMS gas flow to transport the total ion current through the separation gap, the switch time between transmission and separation mode will be limited by the time needed to develop a bi-sinusoidal waveform from zero to a user specified DV amplitude. The rapid alternation between separation and transmission mode on a LC time scale with little loss of ion signal during the switch makes the use of a sine waveform for transmission mode superior over alternative approaches.

Another use of transmission mode is to probe fragmentation of fragile peptides during transit through the FAIMS gap. In the absence of FAIMS, the ion source is situated close to the mass spectrometer inlet and ions can be sucked into the mass spectrometer within a few milliseconds—creating a less likely condition for fragmentation. Ions passing through the FAIMS separation gap can be seen as experiencing fragmentation conditions: frequent collisions between peptides and the molecules of the supporting atmosphere, heat from the FAIMS electrodes (up to 200 degrees C.), and RF heating—all for a period of approximately 50 ms (ion transit time through FAIMS). In select applications the FAIMS fragmentation condition can be controlled to regulate fragmentation of a CV selected precursor (separation mode) or all precursors (transmission mode) and the abundance of associated product ions. A "in FAIMS" fragmentation approach can be seen as an alternative to "in source Collision Induced Dissociation" (CID) where in the latter approach a DC bias is applied to the mass spectrometer inlet capillary to accelerate ions into the first pumping stage of the mass spectrometer to induce fragmentation.

In some applications the desire could be to minimize in FAIMS fragmentation. For such cases it may be useful to have a way to first confirm if the ion fragmentation is occurring during transit inside the FAIMS ion separation gap. Associating fragmentation to FAIMS conditions can be complicated by the inability to transmit pre-cursor and fragment ions simultaneously through FAIMS owing to quadrupole ion filtering behavior of the device in separation mode: the FAIMS device cannot pass a precursor and product ion simultaneously. Thus varying a FAIMS fragmentation parameter and observing a change in the precursor-product ion abundance can be difficult to accomplish. One way to accomplish it could be to study the fragmentation in transmission mode where all ions are passed to the mass spectrometer. The approach, however, will disable the RF waveform and eliminate the contribution of RF heating. However, by applying a sine waveform the contribution of RF heating towards fragmentation can be included and both the precursor and the product ion can be transmitted simultaneously.

Another advantage of transmission mode with a sine waveform is beneficial to native protein analysis. Analyses seeking native features of proteins require preservation of their assembly during transition from condensed phase into gas phase. Preserving such subtle features require the unconventional practice of generating ions in strictly aqueous medium, which presents a difficult ion de-solvation challenge. Users often rely on heated mass spectrometer inlet, which alone is known to be inadequate for de-solvation of ions produced in such aqueous rich condition. One way to improve de-solvation involves extending the mass spectrometer inlet and increasing ion transit time through the heated capillary. The downside of the approach could be an excessive extension of the capillary to achieve any significant de-solvation and an increased ion loss along the extended capillary. However, placing FAIMS between the ion source and the mass spectrometer inlet creates a condition comparable to extending the mass spectrometer inlet but with little loss in ion transmission. The extended ion path can add between 10 ms to 50 ms of transit time depending of the conductance of the mass spectrometer inlet. More importantly, the transport of ions through the FAIMS gap will occur under heated conditions created by the heated FAIMS electrodes (up to 200 degrees C.) and the RF ion heating from the sine waveform. These parameters can be regulated to adjust heat transfer to ions.

Figure 3B:
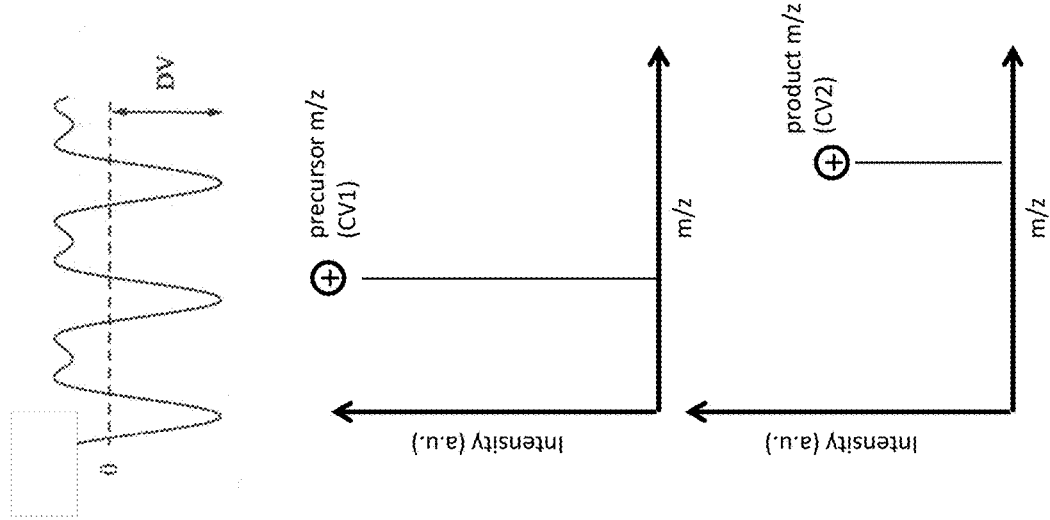
FIG. 3B shows a bisinusoidal waveform during FAIMS separation mode, a mass spectrometry single quadrupole (MS Q1) full scan showing the precursor m/z ions in FAIMS separation mode when both the bisinusoidal waveform and a DC compensation voltage (CV1) are applied, and a MS scan of the product m/z ions in FAIMS separation mode when both the bisinusoidal waveform and DC compensation voltage (CV2) are applied.
Figure 3A:
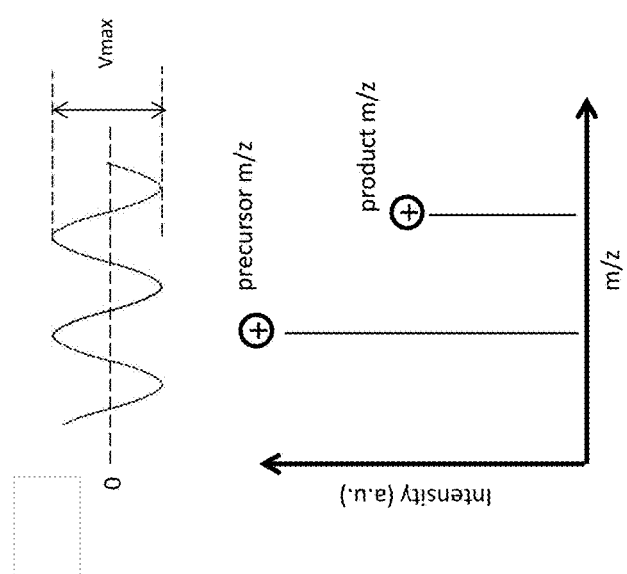
FIG. 3A shows a FAIMS sine waveform of voltage amplitude $V_{max}$ and a mass spectrometry single quadrupole (MS Q1) full scan showing both the precursor m/z ion and product m/z ion during FAIMS transmission mode when only a sine wave is applied.

FIG. 3A (top) shows application of a sine wave of voltage amplitude $V_{max}$ during FAIMS transmission mode. FIG. 3A (bottom) shows a MS scan of both precursor m/z ions and product m/z ions during FAIMS transmission mode when only a sine wave is applied.

FIG. 3B (top) shows application of a bisinusoidal waveform during FAIMS separation mode. FIG. 3B (middle) shows a MS scan of the precursor m/z ions in FAIMS separation mode when both the bisinusoidal waveform and a DC compensation voltage (CV1) are applied. FIG. 3B (bottom) shows a MS scan of the product m/z ions in FAIMS separation mode when both the bisinusoidal waveform and DC compensation voltage (CV2) are applied. The compensation voltages—CV1 and CV2—are different for the two scans in FAIMS separation mode.

Figure 4:
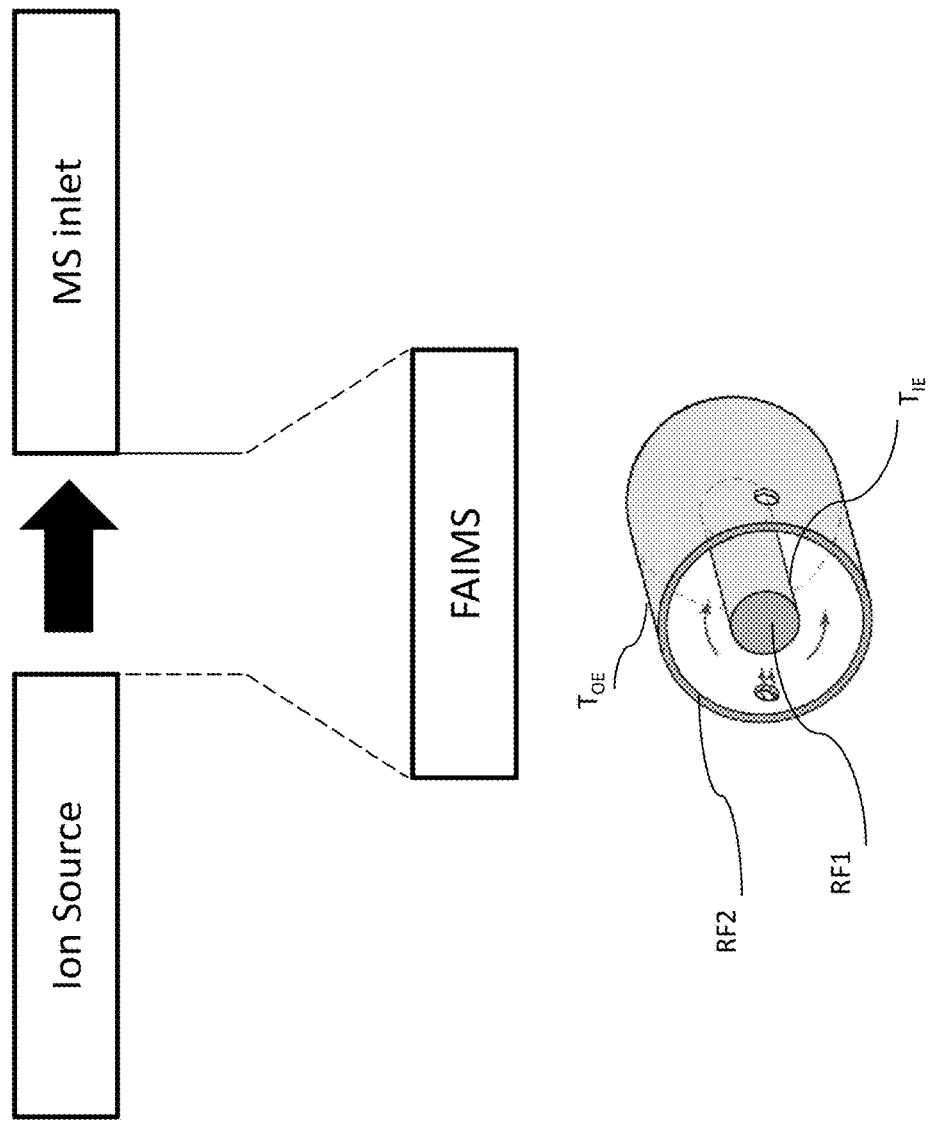
FIG. 4 shows the location of FAIMS between an ion source and the mass spectrometer inlet. The FAIMS electrodes, as shown at the bottom of FIG. 4, can be applied a waveform on the inner (RF1) or the outer (RF2) electrode and heated to different temperatures or to a common temperature.

FIG. 4 (top) shows the coupling of a FAIMS device between an ion source tailored to produce ions for native MS application and the inlet of a mass spectrometer. An ion source tailored to study native protein structures produce ions from strictly aqueous solution and high salt concentration. In the absence of the FAIMS device ions are sampled into the heated mass spectrometer inlet (200° C.) and desolvated prior to mass analysis. However, the desolvation condition is more suited for ions produced from solution containing less aqueous content and the heated capillary alone may be insufficient to desolvate ions for native mass spectrometry study. FIG. 4 (bottom) shows an alternative configuration where a FAIMS device is included between the ion source and the mass spectrometer inlet. Ions can be passed through the FAIMS ion separation gap using transport gas that can be heated to promote desolvation. The transport gas can be heated by heating the Inner Electrode ($T_{IE}$) or Outer Electrode ($T_{OU}$) to approximately 200° C. where the $T_{IE}$ and $T_{OE}$ can be a common temperature or be different. This way of heating ions is termed here as convective heating and is different than ion heating in another embodiment where a sine waveform or any waveform with equal voltage amplitude during the high and low period of the waveform is supplied to either the inner FAIMS electrode (e.g., RF1 applied to the inner electrode in FIG. 4) or outer FAIMS electrode (e.g., RF2 applied to the outer electrode in FIG. 4) to create a non-thermalized condition for ions. During the non-thermal state the temperature of the ion is higher than the temperature of the supporting atmosphere causing internal ion heating. Such heating promotes dissociation of fragile ion-solvent associates.

Figure 5:
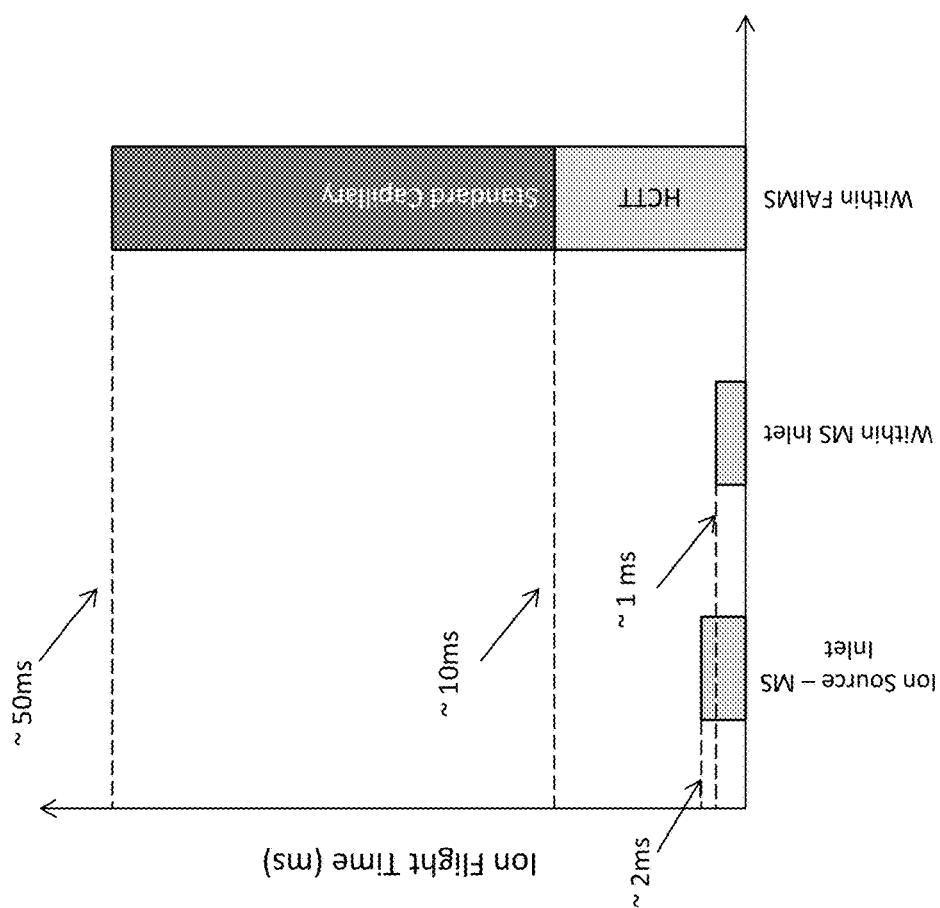
FIG. 5 shows a bar graph highlighting the differences in ion transit time between the ion source and the mass spectrometer inlet, within the mass spectrometer inlet, and within FAIMS.

FIG. 5 show the scale of the ions flight time between an ion source and the mass spectrometer inlet, within the mass spectrometer inlet, and within FAIMS. The ion flight time within FAIMS can vary depending on the type of capillary being used: high capacity transfer tube (HCTT) or standard round bore capillary. The temperature inside these capillaries can range from 100-400° C. but the flight can be short (1-2 ms) limiting the desolvation period. With the inclusion of FAIMS between the ion source and the capillary the desolvation period can be extended between 10 ms (HCTT) and approximately 50 ms (standard capillary). The additive effect of heated ion transport gas (FAIMS), RF ion heating, and long transit time enhance ion desolvation beyond what can be achieved with a capillary alone.

Figure 6:
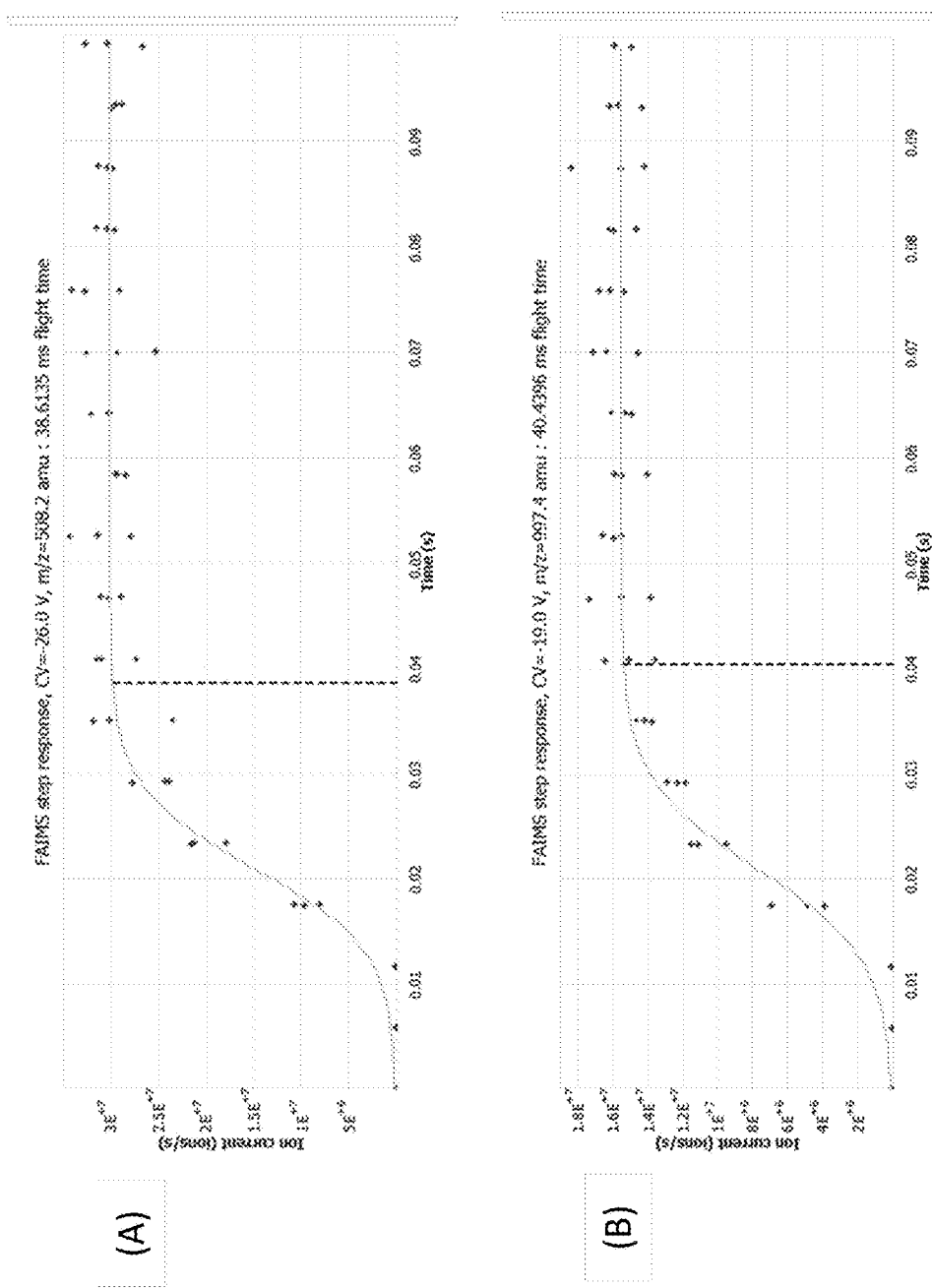
FIG. 6 shows experimental ion flight time of 38.6 ms for m/z 508.2, CV=−26.0V (A) and 40.4 ms for m/z 997.4, CV=−19.0V (B) when a FAIMS device is coupled between the ionization source and a MS equipped with a round bore capillary.

FIGS. 6(A) and 6(B) are experimental data showing the ion flight time when a FAIMS device is coupled between the ionization source (FIG. 4) and a round bore capillary of a mass spectrometer. In FIG. 6(A), ion transit time is plotted for m/z 508 using a 1.5 L/min sampling tube of the round bore capillary. The ion transit time to the round bore capillary for m/z 508 was approximately 39 ms—this is the same amount of time the ions experience desolvation while transiting through the device. In FIG. 6(B), the ion transit time is plotted for m/z 997 using a 1.5 L/min sampling tube of the round bore capillary. The ion transit time to the round bore capillary for m/z 997 was approximately 40 ms—this is also the same amount of time the ions experienced desolvation.

Figure 7:
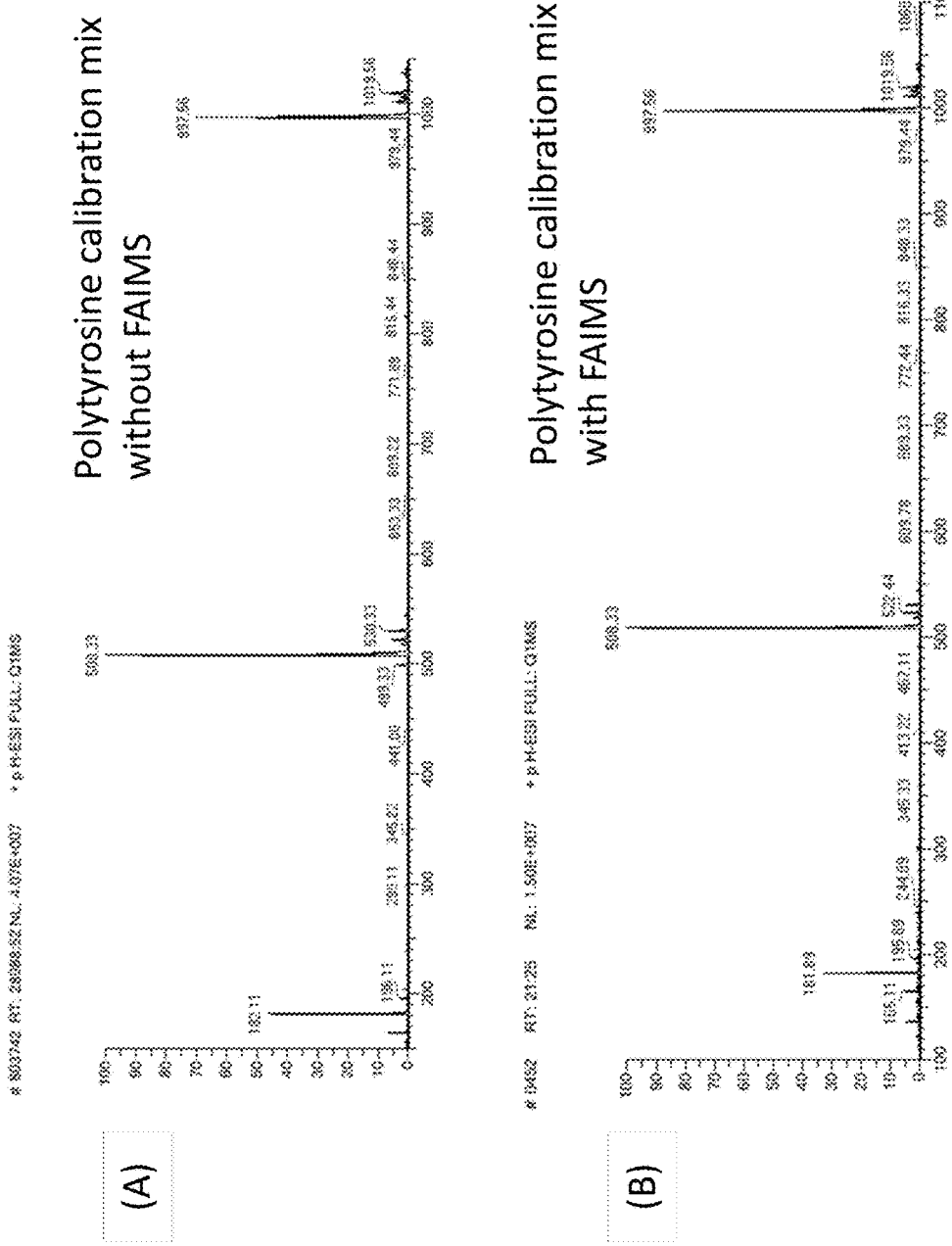
FIG. 7 shows mass spectrometry single quadrupole (MS Q1) full scan for a polytyrosine calibration mixture constituting of three calibrants of nominal m/z 182, 508.2, and 997.5 using a mass spectrometer having a slot-shaped capillary without a FAIMS device between the ion source and the inlet (A) and with a FAIMS device interfaced in transmission mode (B).

FIGS. 7(A) and 7(B) shows spectra for a polytyrosine calibration mixture using a mass spectrometer having a slot-shaped capillary inlet without a FAIMS device interface (FIG. 7(A)) and with a FAIMS device interface in transmission mode (FIG. 7(B)). As seen in FIGS. 6(A) and 6(B)—without or with the FAIMS device interface, respectively—the difference in the signal or measured ion flux is approximately three-fold, with 4.07E+007 ion counts/s in FIG. 6(A) and 1.50E+007 ion counts/s in FIG. 6(B). With the FAIMS device interface, however, there is still sufficient calibrant ion signal to perform mass spectrometry calibration despite the approximately three-fold difference. Thus, sufficient flux is provided with FAIMS coupled to the system to accomplish mass spectrometry calibration, and without requiring removal of any hardware or interruption of ion production.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A FAIMS device that interfaces between an ionization source and a mass spectrometer and operates at or near atmospheric pressure comprising:
    a. inner and outer electrodes having radially opposed surfaces, which define there between a gap through which ions are transported; and
    b. a waveform generator configured to apply a selected one of two distinct periodic waveforms to the electrodes, consisting of: a first waveform characterized by equal high and low amplitudes and periods and a second waveform comprising a bi-sinusoidal waveform superimposed with a DC compensation voltage;
    wherein the device is configured to toggle between a transmission mode of operation in which ions are passed through the device with no spatial separation when the first waveform is applied to the inner and/or outer electrodes and a separation mode of operation in which spatial separation of the ions occurs in the gap when the bi-sinusoidal waveform and DC voltage are applied to the inner and/or outer electrodes.

2. The FAIMS device of claim 1 wherein the toggling between the transmission and separation modes of operation occurs over the course of a liquid chromatography-mass spectrometry (LC-MS) analysis.

3. The FAIMS device of claim 2 wherein during the transmission mode, ion distribution during a precursor scan is visualized for all the ions from the ionization source, providing an instantaneous view of the precursor ions at any point along an LC gradient.

4. The FAIMS device of claim 1 wherein during the transmission mode, RF heating of the ions is induced by varying operational parameters until dissociation or fragmentation occurs in the device.

5. The FAIMS device of claim 4 wherein the varied parameters are one or more of the following: voltage, amplitude, and frequency.

6. The FAIMS device of claim 4 wherein both precursor ions and product ions are simultaneously transmitted through the device.

7. The FAIMS device of claim 6 wherein the ions subjected to the RF heating have a transit time of approximately 50 milliseconds, or up to approximately 100 milliseconds, through the device.

8. The FAIMS device of claim 4 wherein the RF heating, along with an elevated temperature above ambient of the buffer gas in the device, promotes de-solvation of ions produced under aqueous-rich conditions.

9. The FAIMS device of claim 1 wherein during the transmission mode, the ions are transmitted through the device for purposes of calibrating the mass spectrometer instrument without interrupting or stopping ion production.

10. The FAIMS device of claim 1 wherein the first waveform is a sine wave.

11. A method of transmitting and/or separating ions using a FAIMS device that interfaces between an ionization source and a mass spectrometer and operates at or near atmospheric pressure, the method comprising:
    a. providing inner and outer electrodes having radially opposed surfaces, which define there between a gap through which ions are transported;
    b. configuring a waveform generator to apply a selected one of two distinct periodic waveforms to the electrodes, consisting of: a first waveform characterized by equal high and low amplitudes and periods and a second waveform comprising a bi-sinusoidal waveform superimposed with a DC compensation voltage; and
    c. toggling between a transmission mode of operation in which ions are passed through the device with no spatial separation when the first waveform is applied to the inner and/or outer electrodes and a separation mode of operation in which spatial separation of the ions occurs in the gap when the bi-sinusoidal waveform and DC voltage are applied to the inner and/or outer electrodes.

12. The method of claim 11 wherein the toggling between the transmission and separation modes of operation occurs over the course of a liquid chromatography-mass spectrometry (LC-MS) analysis.

13. The method of claim 12 wherein during the transmission mode, ion distribution during a precursor scan is visualized for all the ions from the ionization source, providing an instantaneous view of the precursor ions at any point along the LC gradient.

14. The method of claim 11 wherein during the transmission mode, RF heating of the ions is induced by varying operational parameters until dissociation or fragmentation occurs in the device.

15. The method of claim 14 wherein the varied parameters are one or more of the following: voltage, amplitude, and frequency.

16. The method of claim 14 wherein both precursor ions and product ions are simultaneously transmitted through the device.

17. The method of claim 16 wherein the ions subjected to the RF heating have a transit time of approximately 50 milliseconds, or up to approximately 100 milliseconds, through the device.

18. The method of claim 14 wherein the RF heating, along with an elevated temperature above ambient of the buffer gas in the device, promotes de-solvation of ions produced under aqueous-rich conditions.

19. The method of claim 11 wherein during the transmission mode, the ions are transmitted through the device for purposes of calibrating the mass spectrometer instrument without interrupting or stopping ion production.

20. The method of claim 11 wherein the first waveform is a sine wave.

* * * * *